(12) United States Patent
DeJongh et al.

(10) Patent No.: US 12,332,393 B2
(45) Date of Patent: Jun. 17, 2025

(54) METHOD TO REGISTER AN OPTICAL TRACKING SYSTEM WITH A PARTICLE DETECTOR SYSTEM

(71) Applicants: ProtonVDA LLC., Naperville, IL (US); Board Of Trustees Of Northern Illinois University (NIU), DeKalb, IL (US)

(72) Inventors: Don F. DeJongh, Naperville, IL (US); Ethan A. DeJongh, Naperville, IL (US); Victor Rykalin, Naperville, IL (US); Nicholas Karonis, DeKalb, IL (US); Kirk Duffin, DeKalb, IL (US); Caesar Ordonez, DeKalb, IL (US); John Winans, DeKalb, IL (US)

(73) Assignees: ProtonVDA LLC., Naperville, IL (US); Board Of Trustees Of NIU, Naperville, IL (US)

( * ) Notice: Subject to any disclaimer, the term of this patent is extended or adjusted under 35 U.S.C. 154(b) by 434 days.

(21) Appl. No.: 17/970,240

(22) Filed: Oct. 20, 2022

(65) Prior Publication Data
US 2023/0126392 A1 Apr. 27, 2023

Related U.S. Application Data

(60) Provisional application No. 63/270,328, filed on Oct. 21, 2021.

(51) Int. Cl.
*G01T 5/08* (2006.01)
*G01T 1/16* (2006.01)
*G01T 1/29* (2006.01)

(52) U.S. Cl.
CPC .............. *G01T 5/08* (2013.01); *G01T 1/1603* (2013.01); *G01T 1/2978* (2013.01)

(58) Field of Classification Search
CPC ....... G01T 1/1603; G01T 1/2927; G01T 5/08; G01T 1/29
(Continued)

(56) References Cited

U.S. PATENT DOCUMENTS 8,445,851 B2 * 5/2013 Rousso .................. A61B 5/417
250/363.04
8,586,932 B2 * 11/2013 Rousso ................ A61B 5/4076
250/361 R
(Continued)

*Primary Examiner* — William D Titcomb
(74) *Attorney, Agent, or Firm* — Invent Capture, LLC.; Samuel S. Cho

(57) ABSTRACT

A novel method and a related system are configured to place measured trajectories into a voxel space, which moves with respect to a particle detector system. The trajectories are measured in a detector reference frame. The voxel space, typically fixed with respect to the object being imaged, is tracked optically with markers and a camera system. A decipherable correlation is established between a set of markers and a set of detector elements. This correlation provides coordinate transformation definitions to place the trajectories into the voxel space in medical imaging, treatment planning, and/or therapeutic applications. The novel method provides a clever process to register an optical tracking system with a particle detector system, which improves quality assurance, accuracy, speed, and operating cost efficiencies of ion, particle, and/or radiation-based imaging, treatment planning, or therapies. This novel method may be utilized in proton imaging, helium imaging, other ion-based imaging, or x-ray imaging.

10 Claims, 11 Drawing Sheets

An example of proton imaging with tracking and residual range measurement for each proton

(58) Field of Classification Search
USPC .......................................................... 382/128
See application file for complete search history.

(56) References Cited

U.S. PATENT DOCUMENTS

| | | | | |
|---|---|---|---|---|
| 8,766,180 B2* | 7/2014 | Karonis | ................... | G01T 1/208 |
| | | | | 250/306 |
| 9,316,743 B2* | 4/2016 | Rousso | ................... | G01T 1/1647 |
| 2008/0042067 A1* | 2/2008 | Rousso | ................ | A61B 6/4258 |
| | | | | 250/363.04 |
| 2008/0230702 A1* | 9/2008 | Rousso | ................ | A61B 6/4258 |
| | | | | 250/363.02 |
| 2014/0151563 A1* | 6/2014 | Rousso | ................ | G01T 1/1603 |
| | | | | 250/362 |
| 2014/0367569 A1* | 12/2014 | Karonis | ................... | G01T 1/29 |
| | | | | 250/306 |
| 2016/0338654 A1* | 11/2016 | Dejongh | ................... | G01T 1/29 |
| 2017/0059719 A1* | 3/2017 | Kross | ................... | G01T 1/20187 |

* cited by examiner

An example of proton imaging with tracking and residual range measurement for each proton

100

An example of proton CT imaging with proton data from multiple angles placed in a single 3D voxel coordinate grid

200

301　　　　　　　　　　　　　　302

A camera system tracking markers in its native coordinate system and a rigid body coordinate system which become correlated to generate a proton trajectory in a voxel grid

300

An optical tracking system installed on a proton imaging system, wherein protons are emitted from the left and cameras with LED lights utilize retro-reflective markers

400

A gantry configuration example, wherein the patient is stationary on a couch and proton enters the system from any angle around the axis of the patient

500

Vertical scintillating fiber detectors installed in a tracking frame, wherein scintillation light generated from proton tracks is guided towards the top and measured with photodetectors

600

A close-up view of scintillating fibers adjacent to frame, with each fiber and each optical marker having a definite position relative to the frame

700

A flowchart showing an implementation example that utilizes a camera system to place a measured trajectory into a voxel system

800

A flowchart showing an alternate implementation example that utilizes a camera system to place a measured trajectory into a voxel system

900

Markers placed on tracking plane for a quick relational check of two coordinate systems from the proton imaging system and the camera system

1000

1100A

1100B

An example for registering an optical tracking system with a particle detector system that utilizes PET detectors in proton therapy

METHOD TO REGISTER AN OPTICAL TRACKING SYSTEM WITH A PARTICLE DETECTOR SYSTEM

BACKGROUND OF THE INVENTION

The present invention generally relates to one or more medical imaging and treatment planning systems. More specifically, various embodiments of the present invention relate to novel methods to register an optical tracking system with a particle detector system to improve quality assurance, accuracy, speed, and related operating cost efficiencies of ion, particle, and/or radiation-based imaging, treatment planning, or therapies. Furthermore, various embodiments of the present invention also relate to methods and systems that are configured to place measured trajectories into a voxel space for optimized medical imaging reconstructions. While most embodiments of the invention relate to proton-based imaging for medical treatment planning or therapies, the novel techniques disclosed herein can also be applied to imaging with other ions (e.g. helium, carbon, etc.) or x-rays in other embodiments of the invention.

In radiation therapy, protons provide a superior dose distribution compared to x-rays, with a relatively low dose deposition in the entrance region (i.e. also known as the "plateau"), followed by a steep increase to a dose peak (i.e. a Bragg peak) and an even steeper distal dose fall-off. This well-defined range is the main advantage of proton therapy, delivering less dose to healthy tissues, thus fewer complications and side effects and a better quality of life, even if the proton therapy does not necessarily exhibit an increased biological effectiveness relative to other available radiation therapies. However, the steep distal dose gradient and finite range of proton beams utilized in proton therapy can also be a significant disadvantage, when the actual position of proton beams is uncertain.

In a conventional proton therapy environment, such positional uncertainties may arise from a variety of factors. For instance, the conventional utilization of x-ray imaging for treatment planning to obtain a map of relative stopping power (RSP) of tissues (i.e. compared to water) may be inaccurate due to the differences in the dependence of x-ray attenuation and proton energy loss on tissue composition involving electron density and atomic number. This inaccurate mapping of tissue RSPs then results in an inherently-inaccurate conversion of x-ray Hounsfield units to proton RSP. Furthermore, positional uncertainties for proton therapy can also originate from the particularity of a patient setup (e.g. alignment of the patient to isocenter, deformations from non-rigid changes (e.g. shoulder movements)), an inadvertently-changed position of a tumor due to the patient's breathing cycle, a patient's anatomical changes during the course of fractionated treatments, or a combination thereof.

Conventional treatment planning procedures for proton therapy can take these uncertainties into account with mitigation measures, such as adding uncertainty margins, selecting beam angles tangential to organs at risk, and robust optimization. In addition, by utilizing additional dose delivery techniques such as Pencil Beam Scanning (PBS) and intensity modulation, the resulting treatment plans may become sufficiently robust to the uncertainties. However, these conventional mitigation measures inherently increase the high-dose treatment volume and can preclude use of the most advantageous beam angles. In order to improve the benefit-to-risk ratios of proton therapy while reducing related operational costs and diagnostics and treatment durations, additional innovations in the fields of proton beam-based image guidance and image reconstruction techniques may be advantageous. This is particularly the case for hypo-fractionated treatments who can benefit from more conformal dose distributions and a higher standard of safety during the high-dose delivery in each treatment.

By innovatively encompassing both proton radiography (pRad) and proton computer tomography (pCT), it may be possible to reduce range uncertainties with pCT, while providing a fast and efficient patient setup and range check along a beam's eye view just before treatment. In an intensity-modulated proton therapy (IMPT), two or three proton beams are combined during each treatment to deliver individual dose distributions that add up to a highly conformal dose in the target volume and respect the tolerance doses of organs at risk (e.g., eyes, cranial nerves, parotid glands). The steep distal dose gradient of proton beams is particularly helpful in protecting these vulnerable organs at risk. Therefore, a reduction in range uncertainties would offer a great clinical advantage in these patients.

Proton imaging has a potential to resolve current challenges associated with range inaccuracies in proton therapy. In particular, proton CT (pCT) may be able to substantially reduce the uncertainties of treatment planning by directly measuring an RSP (i.e. the tissue property determining proton energy loss) without being affected by image artifacts and with much lower dose to the patient than comparable x-ray images. In addition, proton radiography (pRad) can provide the capability to verify the range of individual proton beams before treatment. A combined utilization of pCT and pRad exhibits a promising potential for clinicians to fully utilize the advantages of proton radiotherapy.

FIG. 1 shows an example (100) of proton imaging, with tracking and residual range measurements for each proton. A proton radiograph would resemble the rightmost image (104) in FIG. 1, which displays ranges through the patient vs. transverse position. The protons are delivered with pencil beam scanning, and thus emerge from a focal point with a diverging pattern (103). The steering of the pencil beam is typically calibrated to be directed at coordinates in an isocentric plane between the tracking detectors (101). The known steering and diverging pattern (103) can be used to register the tracker coordinate systems with the isocentric coordinate system.

As illustrated in FIG. 1, proton imaging uses tracking detectors (101) to measure the transverse positions of individual protons before and after the patient (102), and a residual range detector to determine the proton energy absorbed within the patient (102). A two-dimensional pRad image uses a single projection angle, directly quantifying proton range through the patient (102) rather than integrated x-ray attenuation. A three-dimensional pCT image measures the three-dimensional (3D) RSP map of the patient by acquiring proton histories from a full set of projection angles. Proton trajectories deviate from straight lines due to multiple Coulomb scattering, thus blurring images.

ProtonVDA is a medical imaging and equipment developer, which is also a co-Applicant to the present invention. By utilizing ProtonVDA's innovative imaging methods and related systems currently in development, this image blurring problem may be resolved by measuring each proton trajectory individually to estimate its most likely path, along with its energy loss quantified as water-equivalent path length (WEPL) and then applying iterative reconstruction algorithms. In one instance, ProtonVDA's medical imaging system currently in development is compact, monolithic, scalable to large field sizes (e.g. 40×40 $cm^2$), and utilizes fast-scintillator technology. Images are typically reconstructed with iterative algorithms executed through parallel processing on a scalable number of graphics processing units (GPUs) and/or central processing units (CPUs) in one or more servers or other computing devices. In a preferred implementation of the system, data acquisition and image reconstruction are automatically combined to promptly display images accurately in terms of water equivalent thickness (WET) or RSP. This novel medical imaging system in development is also capable of automatically aligning itself to isocenter. A transformation from tracker coordinates to isocenter coordinates may be derived using knowledge of the steering of pencil beams to calibrated locations in the isocenter plane which is defined relative to the PBS system. The isocenter plane is transverse to the central pencil beam and at a defined distance from a focal point. Because pencil beams diverge from this focal point, a pattern of locations of pencil beam spots in a tracker plane defines the location of the tracker plane in isocenter coordinates.

FIG. 2 shows an example of multi-angle proton data acquisitions (201, 202, 203) in a proton computed tomography (pCT) along a rotational axis for an object undergoing proton imaging. Proton CT requires acquisition of proton data from a full set of angles, with either an object rotating with fixed detectors, or a fixed object with the imaging system rotation around the object. Protons from one or more directions could also be used to update a previous 3D map of proton stopping power. These applications require protons taken at various angles to be place into a common voxel grid. As shown in this example (200), protons and their pathways, as indicated by three arrows (i.e. A, B, C), are acquired with the object at different angles relative to the detectors. For image reconstruction, all proton trajectories from multiple angles are placed in a single 3D voxel coordinate grid, as shown on the rightmost image (204) in FIG. 2. Markers on the rotating platform can be utilized to determine the rotation angle.

As shown in FIG. 2, the challenge for pCT over pRad is to acquire protons through the object at many different angles and put all proton trajectories into a single 3D coordinate grid (i.e. voxel space) for image reconstruction. The iterative algorithm then adjusts the RSPs of the voxels touched by the protons to match the residual ranges of the protons. The transformation from detector coordinates to the reconstruction grid can rely on known movements of rotational actuators and can also incorporate optical tracking. A preferred standard voxel size is 1 mm$^3$, which is matched to our expected spatial resolution and also sets the scale for the 0.5 mm accuracy requirement for the optical tracking.

In medical imaging applications, optical tracking is able to measure rotational movements directly, and the stability of a patient positioning system (PPS) and proton computed tomography (pCT) detectors can be verified. Furthermore, optical tracking can function along with a laser alignment system at a treatment isocenter, and also allows utilization of actual movements without being dependent on the accuracy or the stability of the rotational axis.

It is also possible to use one or more pRad images to iteratively update a pre-existing 3D RSP map for an object. In this case, there may be rotations between pRad images, and the ability to place protons from the different pRad data sets into the voxel space becomes as critical as for pCT images. High-quality pCT image reconstruction requires the position of a rotation axis to be stable and be detected at a resolution finer than 0.5 mm. In a research and development environment, this condition is achieved by integrating both the detectors and a rotating phantom stage into a single platform. For instance, an object can be placed on a rotational stage, which is mechanically integrated with the detector system and rotating at a known rate around an axis. This axis is situated in a stable location and orientation relative to detectors associated with the detector system. In this prototypical setting, the orientation of the object can be determined from a single angle that increases with a stable known rate with time.

However, in a clinical setting, this type of singularly-integrated mechanical structure is not commercially viable for practical usage. As a case in point, in a typical clinical setting, the patient positioning system (PPS) is not mechanically linked to the pCT system. A patient undergoing medical imaging may be lying on a couch with a gantry and detector system rotating around the couch. In another instance, the patient may be in a rotating chair independently placed on the floor.

Yet in another instance, conventional rotational systems deployed in a clinical environment may not have a stable axis of rotation, and orientation may not be described accurately by a single angle. Furthermore, determining the orientation of the object from the single angle relies on the accuracy of encoders to ensure that rotational movements have occurred as intended, which may not always be reliable or accurate.

In all such instances, the quality assurance burden to understand the relationship with the PPS and the pCT system is time-consuming and laborious, which reduces operational and cost efficiencies in a commercialized clinical environment for patient diagnosis and treatment. Although careful alignments of the rotation axis and detectors may theoretically render desirable results, quality assurance difficulties are likely to cause time delays, cumbersome preparation procedures, and cost inefficiencies in the clinical setting.

In order to overcome the drawbacks of the singularly-integrated mechanical structure deployed in a prototype environment, it may be advantageous to standardize and unify the registration of a camera-based optical coordinate system with a detector coordinate system in medical imaging applications. A typical optical tracking system is able to track movements within its own coordinate system, which may not necessarily be fixed in place from one operational session to another. Furthermore, a typical pCT detector system has a separate coordinate system, which can be related to the treatment isocentric coordinate system by observing a set of diverging pencil beams.

Therefore, in order to make the combined utilization of pCT and pRad more practical in a clinical medical imaging environment, it may be desirable to coherently correlate and register these two disparate coordinate systems (i.e. from the camera-based optical coordinate system and the pCT imaging detector system) in a unified coordinate system of voxel coordinates for pCT image reconstructions.

In addition, it may also be desirable to devise a novel method and a related system to determine the orientation of an object relative to detectors in a clinically-practical and efficient manner in medical tomographic imaging applications that utilize protons, helium, carbon, or x-rays.

Furthermore, it may also be desirable to devise a novel method and a related system to measure movements with a set of cameras arranged in a treatment room, and simultaneously tracking reflective markers mounted on proton imaging detectors and an object positioning system to alleviate the quality assurance requirement on the stability of the rotation axis.

Moreover, it may also be desirable to devise a novel method to register an optical tracking system with a particle detector system to improve quality assurance, accuracy, speed, and related operating cost efficiencies of ion, particle, and/or radiation-based imaging, treatment planning, or therapies.

In addition, it may also be desirable to devise a novel method and a related system that are configured to place measured trajectories into a voxel space for optimized medical imaging reconstructions.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

The present invention discloses one or more novel methods and systems to place measured trajectories into a voxel space that moves with respect to a detector system. The trajectories are measured in a detector reference frame. The voxel space, which is fixed with respect to the object being imaged, is tracked optically with markers and a camera system. A decipherable correlation is established between a set of markers and a set of detector elements. This enables the definition of a transformation to place the trajectories into the voxel space in medical imaging, treatment planning, and/or therapeutic applications.

Furthermore, the present invention also discloses one or more novel methods to register an optical tracking system with a particle detector system to improve quality assurance, accuracy, speed, and related operating cost efficiencies of ion, particle, and/or radiation-based imaging, treatment planning, or therapies. These novel methods and systems can be deployed for proton imaging as well as helium imaging, other ion-based imaging, or x-ray imaging.

In one embodiment of the invention, a method for registering an optical tracking system with a particle detector system in a common voxel coordinate grid to improve quality assurance, accuracy, speed, and operating cost efficiencies of a medical imaging process is disclosed. This method comprises the steps of: (1) defining, with a camera system as the optical tracking system, a rigid body from a first set of markers on an object support and a second set of markers on a tracking frame; (2) obtaining, with the camera system, a time-dependent coordinate transformation from camera coordinates to rigid body coordinates; (3) obtaining, with the camera system, a coordinate transformation from the camera coordinates to tracker coordinates of the tracking frame; (4) calibrating, with a proton imaging system as the particle detector system, locations of trackers in an isocentric coordinate system; (5) obtaining, with the proton imaging system, a coordinate transformation from the tracker coordinates to isocentric coordinates in the isocentric coordinate system; (6) obtaining, with the camera system and the proton imaging system, a coordinate transformation from the camera coordinates to the isocentric coordinates; (7) obtaining, with the camera system, a time-dependent coordinate transformation from the rigid body coordinates to the isocentric coordinates; (8) defining voxel coordinates of the common voxel coordinate grid to coincide with the isocentric coordinates at a beginning of measurement, wherein the voxel coordinates move with the rigid body; (9) obtaining a time-dependent coordinate transformation from the isocentric coordinates to the voxel coordinates; (10) measuring, with the proton imaging system, a proton trajectory in the tracker coordinates; (11) placing, with the proton imaging system, the proton trajectory into the isocentric coordinates; and (12) placing the proton trajectory into the voxel coordinates of the common voxel coordinate grid by utilizing the time-dependent coordinate transformation from the isocentric coordinates to the voxel coordinates and the proton trajectory in the isocentric coordinates.

In another embodiment of the invention, a method for registering an optical tracking system with a particle detector system in a common voxel coordinate grid to improve quality assurance, accuracy, speed, and operating cost efficiencies of a medical imaging process is disclosed. This method comprises the steps of: (1) defining, with a camera system as the optical tracking system, a rigid body from a first set of markers on an object support and a second set of markers on a tracking frame; (2) obtaining, with the camera system, a time-dependent coordinate transformation from camera coordinates to rigid body coordinates; (3) obtaining, with the camera system, a coordinate transformation from the camera coordinates to tracker coordinates of the tracking frame; (4) calibrating, with a proton imaging system as the particle detector system, locations of trackers in an isocentric coordinate system; (5) obtaining, with the proton imaging system, a coordinate transformation from the tracker coordinates to isocentric coordinates in the isocentric coordinate system; (6) obtaining, with the camera system and the proton imaging system, a coordinate transformation from the camera coordinates to the isocentric coordinates; (7) obtaining, with the camera system, a time-dependent coordinate transformation from the rigid body coordinates to the isocentric coordinates; (8) defining voxel coordinates of the common voxel coordinate grid to coincide with the isocentric coordinates at a beginning of measurement, wherein the voxel coordinates move with the rigid body; (9) obtaining a time-dependent coordinate transformation from the isocentric coordinates to the voxel coordinates; (10) measuring, with the proton imaging system, a proton trajectory in the tracker coordinates; (11) placing, with the proton imaging system, the proton trajectory into the isocentric coordinates (12) and; (13) placing the proton trajectory into the voxel coordinates of the common voxel coordinate grid by utilizing the time-dependent coordinate transformation from the isocentric coordinates to the voxel coordinates and the proton trajectory in the isocentric coordinates.

DETAILED DESCRIPTION

Figure 1:
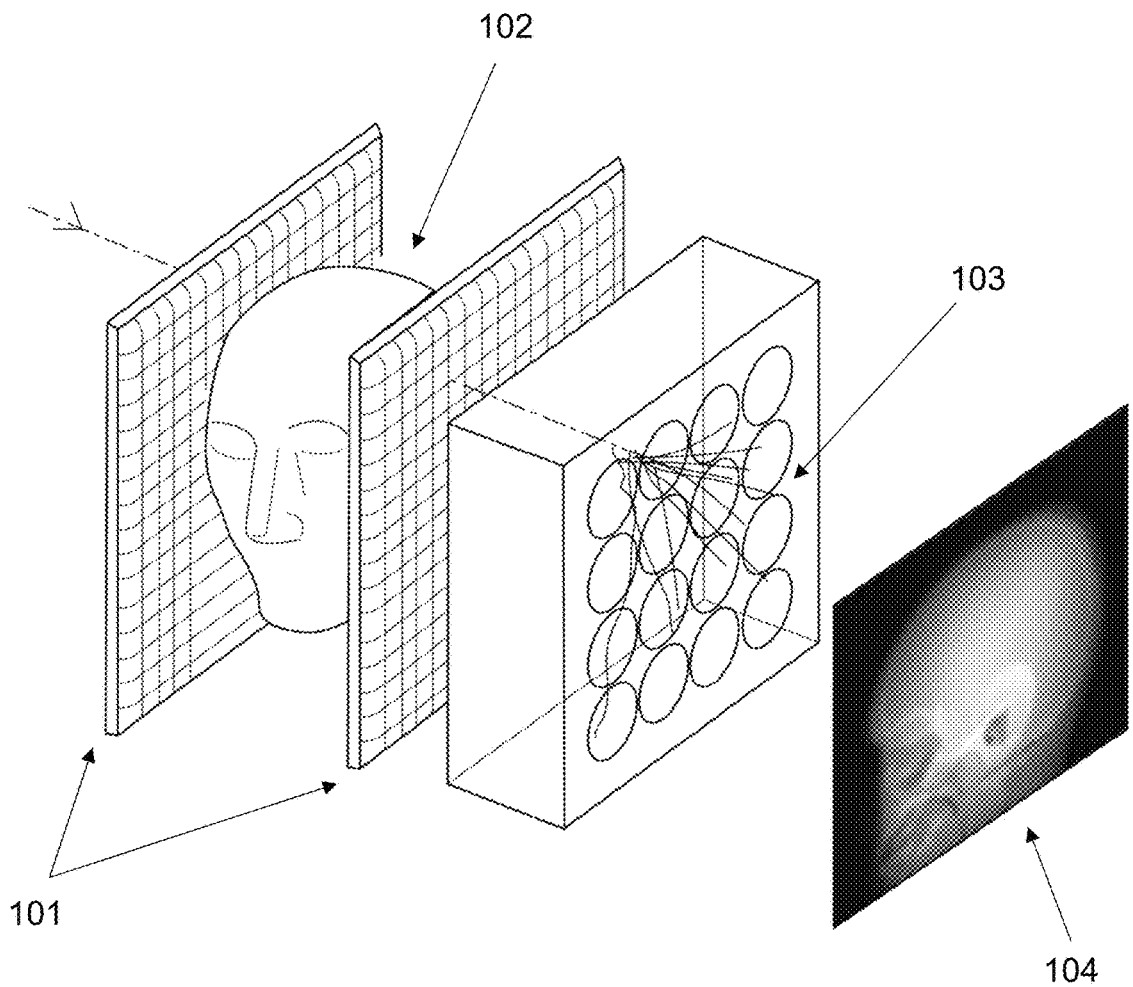
FIG. 1 shows an example of proton imaging, with tracking and residual range measurements for each proton.
Figure 2:
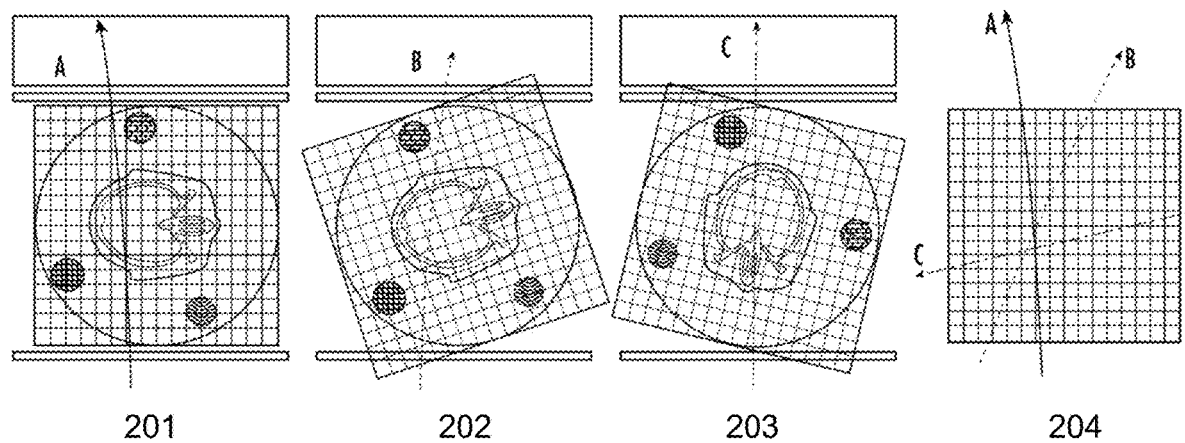
FIG. 2 shows an example of multi-angle proton data acquisitions in a proton computed tomography (pCT) along a rotational axis for an object undergoing proton imaging.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more methods and systems that can determine the orientation of an object relative to detectors in a clinically-practical and efficient manner in medical tomographic imaging applications. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention does not inherently indicate any particular order nor imply any limitations in the invention.

For the purpose of describing the invention, a term herein referred to as "pencil beam scanning," or "PBS," is defined as a precision dose-delivery technique that scans narrow proton particle beams across a target. Compared to using standard broad proton beams emitted by conventional proton therapy machines, the PBS may reduce unnecessary radiation exposure to unintended surrounding cells (e.g. non-cancerous cells near targeted tumor cells) through computer-guided precision beam steering.

One aspect of an embodiment of the present invention is to determine the orientation of an object relative to detectors in a clinically-practical and efficient manner in medical tomographic imaging applications.

Another aspect of an embodiment of the present invention is to provide a novel method and a related system to measure movements with a set of cameras arranged in a treatment room, and simultaneously tracking reflective markers mounted on proton imaging detectors and an object positioning system to alleviate the quality assurance requirement on the stability of the rotation axis.

Yet another aspect of an embodiment of the present invention is to provide a method to register an optical tracking system with a particle detector system to improve quality assurance, accuracy, speed, and related operating cost efficiencies of ion, particle, and/or radiation-based imaging, treatment planning, or therapies.

Yet another aspect of an embodiment of the present invention is to provide a novel method and a related system that are configured to place measured trajectories into a voxel space for optimized medical imaging reconstructions.

Optical tracking of rigid bodies is used extensively in the medical field. For example, markers can be attached to surgical needles for guided biopsies or to ultrasound probes to enable the reconstruction of 3D ultrasound images. Optical tracking of rigid bodies are commercially available as low-cost solutions, and typically incorporate cameras, markers, and software for 3D tracking. Passive markers simply reflect light back to a tracking camera and can be arranged in a certain unique pattern so that the tracking camera can identify the markers. If a known object is seen with two cameras and the geometry between the cameras is fixed and known, the object can be located in a 3D reference frame using stereophotogrammetry. Commercial systems, such as Optitrack, include calibration wands and software to establish the geometry between the cameras, and establish a 3D coordinate system for the camera system. When passive markers are rigidly related to each other and are identified as a rigid object in the field of view (FOV) of several cameras, the system will track that rigid body, provided enough markers are seen by at least two of the cameras at any given moment.

Figure 3:
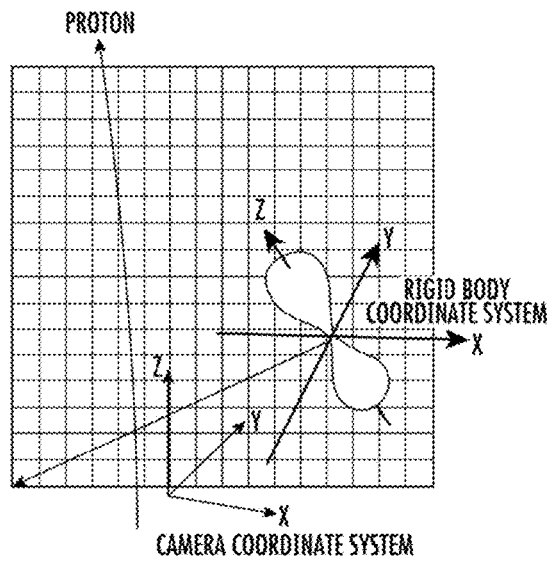
FIG. 3 shows a camera system tracking markers in its own self-defined (i.e. native) camera coordinate system and a rigid body coordinate system, which become correlated to generate a proton trajectory in a voxel grid.
Figure 3:
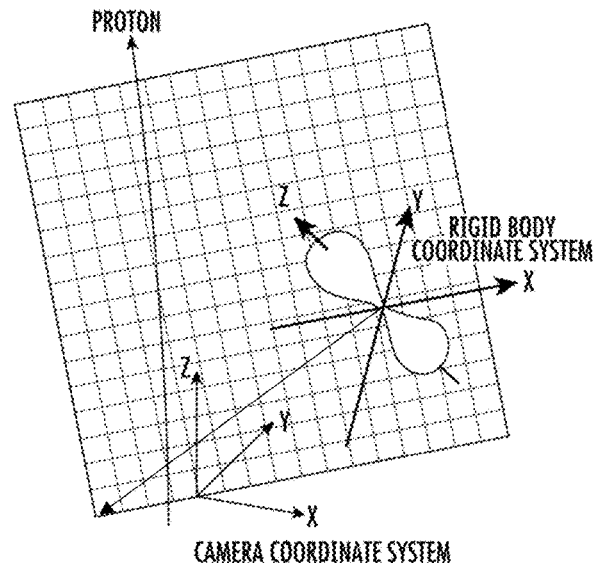

FIG. 3 shows an example (300) of a camera system tracking markers in its own self-defined native coordinate system and a rigid body coordinate system, which become correlated to generate a proton trajectory in a voxel grid. Three or more markers can define a rigid body with its own coordinate system, track the origin of the rigid body coordinate system, and provide a time-dependent transformation from the camera coordinate system to the rigid body coordinate system. A voxel grid can be defined as chosen by the user, with a fixed transformation from the rigid body coordinate system to the voxel coordinate grid. If the tracker coordinate system can be related to the camera coordinate system, the proton trajectory can be placed into the voxel grid.

As illustrated in two diagrams (301, 302) in FIG. 3, the camera system assigns an origin and an orientation to each rigid body. This establishes a rigid body internal coordinate system attached to the rigid body at this origin, as illustrated, for example, in the first diagram (301). The camera system tracks the position and orientation of the rigid body in its own internal coordinate system, as illustrated, for example, in the second diagram (302). The orientation may typically be provided as Euler angles or quaternions. Quaternions have some advantages over Euler angles, which are often used to represent 3D rotations. Quaternions are often preferred because of their compactness and immunity to gimbal lock when passing through certain orientations. Position and orientation information enables coordinate transformations between camera coordinates to rigid body coordinates that update as the object moves, as shown in the two diagrams (301, 302). The most common movement is a rotation, but the system also works well for other movements, including wobbles, horizontal translations, and vertical translations.

If the rigid body is attached to the rotating platform, the voxel grid moves with the rigid body, and a fixed transformation from the rigid body coordinate system to the voxel space occurs as shown, for example, in the second diagram (302). It is therefore possible to derive a transformation from the camera coordinate system to the voxel space that follows the movements of the rigid body.

In a preferred embodiment of the invention, proton trajectories are measured in the coordinate system of the tracking system. In order to place these trajectories into the voxel grid, it is necessary to find the relationship between the tracking coordinate system and the camera coordinate system, and from there to the voxel space, using the coordinate transformation for the time of the proton detection. Once all of information necessary for a full transformation is available, proton trajectories may be transformed from the tracking system to the voxel grid with standard methods. For example, the trajectory may be represented as a series of points connected by lines or curves, and each individual point may be transformed into the voxel space.

In the preferred embodiment of the invention, coordinate transformations can be executed using standard transformation methods. For example, homogeneous coordinates are a well-established representation for systems involving transformations of lines and planes. A point in n-dimensional space is represented by n+1 values, unique to a scale factor. An important result of projective geometry is that any three-dimensional (3D) projective transformations, such as translations, rotations, scaling, skews, and perspective projections, can be represented as a 4×4 matrix. Homogeneous points are transformed by multiplication with a transformation matrix. Because of the matrix representation, sequences of projective transformations can be concatenated into a single projective transformation through matrix multiplication.

In the preferred embodiment of the invention, a choice of placement of the voxel grid is made at a starting time, such as t=0. This choice of placement of the voxel grid can be made for an operator's convenience. For example, if the tracking system is aligned to isocenter, the voxel grid can be chosen to align to isocenter and results for a patient can be presented directly in isocenter coordinates in the orientation at which the patient was positioned before imaging.

Figure 4:
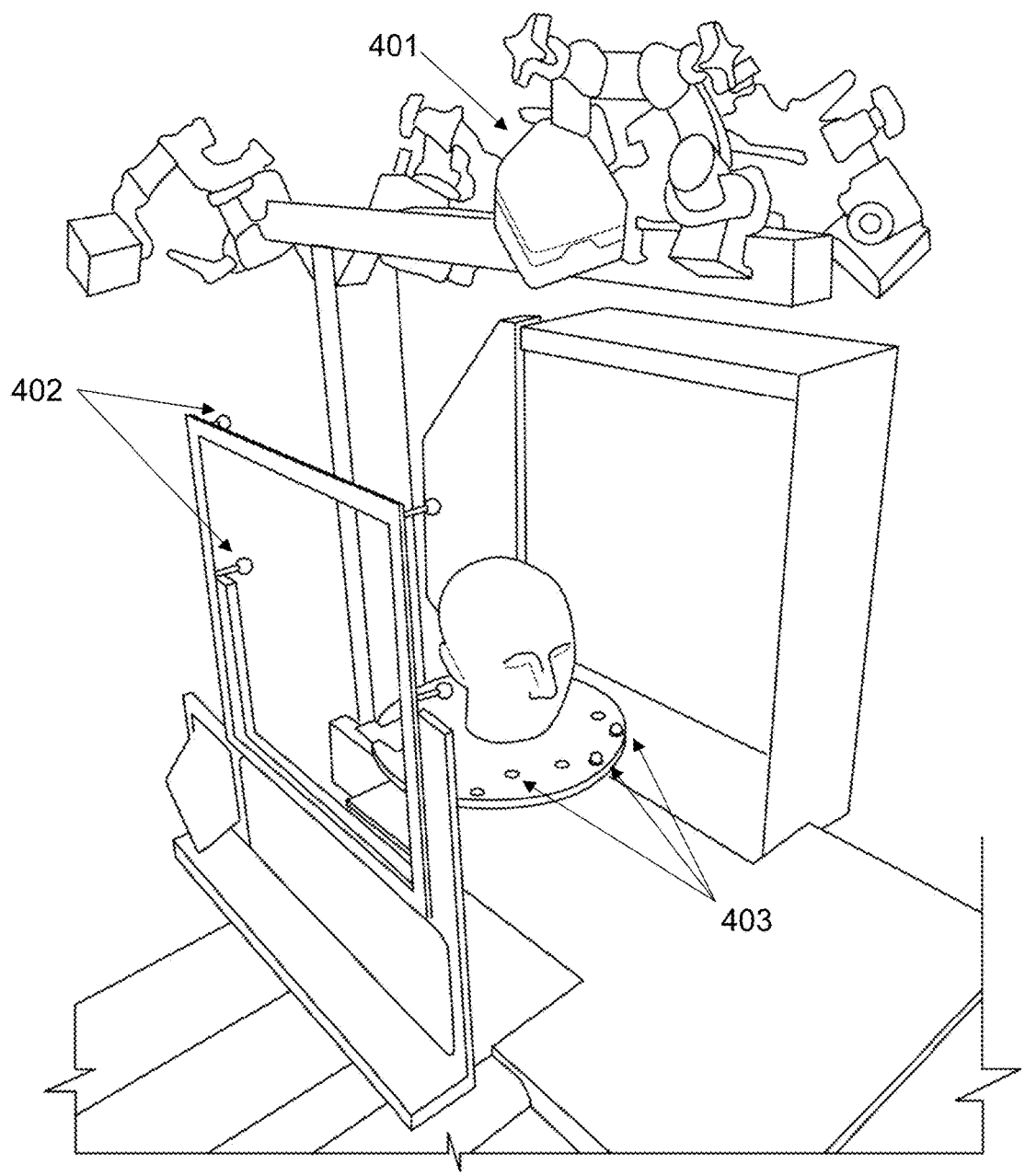
FIG. 4 shows an optical tracking system installed on a prototype proton imaging system, wherein protons are emitted from the left and cameras with LED lights utilize retro-reflective markers, in accordance with an embodiment of the invention.

FIG. 4 shows an example (400) of an optical tracking system installed on prototype proton imaging system, in accordance with an embodiment of the invention. In this embodiment of the invention, protons enter the system from the left. For a simplified clarity of the illustration, the optical tracking system in FIG. 4 is shown with some sensitive tracking elements removed from the frame for the upstream tracker. Cameras equipped with LED lights (401) view markers (402, 403) with retro-reflective coating. The cameras view the first set of markers (403) on the rotating platform with the object to be imaged, and also view the second set of markers (402) attached to the upstream tracking plane frame.

The optical tracking system illustrated in FIG. 4 is an example of a detector system (e.g. pCT imaging detector system) combined with an optical tracking system, in accordance with an embodiment of the invention. The first set of retro-reflective markers (403) on a rotating platform between the tracking planes define a first rigid body. The second set of retro-reflective markers (402) on the frame of the upstream tracker define a second rigid body. A set of four cameras equipped with LED lights (401) can view the markers and track movements of the rigid bodies. A horizontal beam arriving from the left scans the rotating object. The retro-reflective markers (402) on the tracking planes can be used to relate the detector coordinate system and the camera coordinate system.

Figure 5:
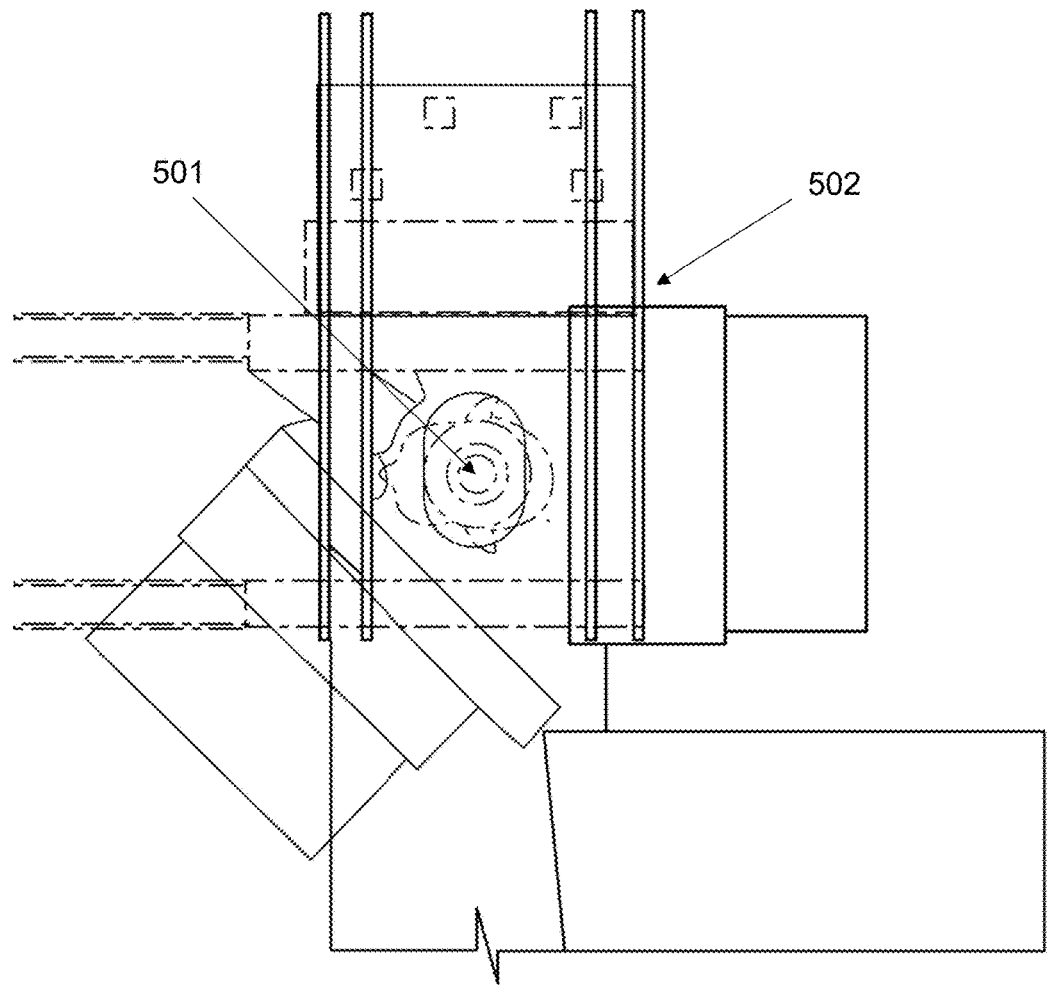
FIG. 5 shows a gantry configuration where the patient is stationary on a couch, and the protons enter the system from any angle around the axis of the patient, in accordance with an embodiment of the invention.

FIG. 5 shows a gantry configuration (500) where the patient (501) is stationary on a couch, and the protons enter the system from any angle around the axis of the patient, in accordance with an embodiment of the invention. This is an alternative gantry-based configuration, in which the patient is stationary on a couch, and the proton beam can scan the patient from any angle.

The configuration (500) presented in FIG. 5 is conceptually equivalent to the configuration (400) in FIG. 4 in that the voxel space remains fixed with respect to the object and the detectors and the proton beam rotate around the couch with the gantry (502), and there is therefore a rotation relative to the object. Retro-reflective markers could be placed on the couch and the tracking detectors. The camera system can move with the detector system or can be stationary with the room.

Figure 6:
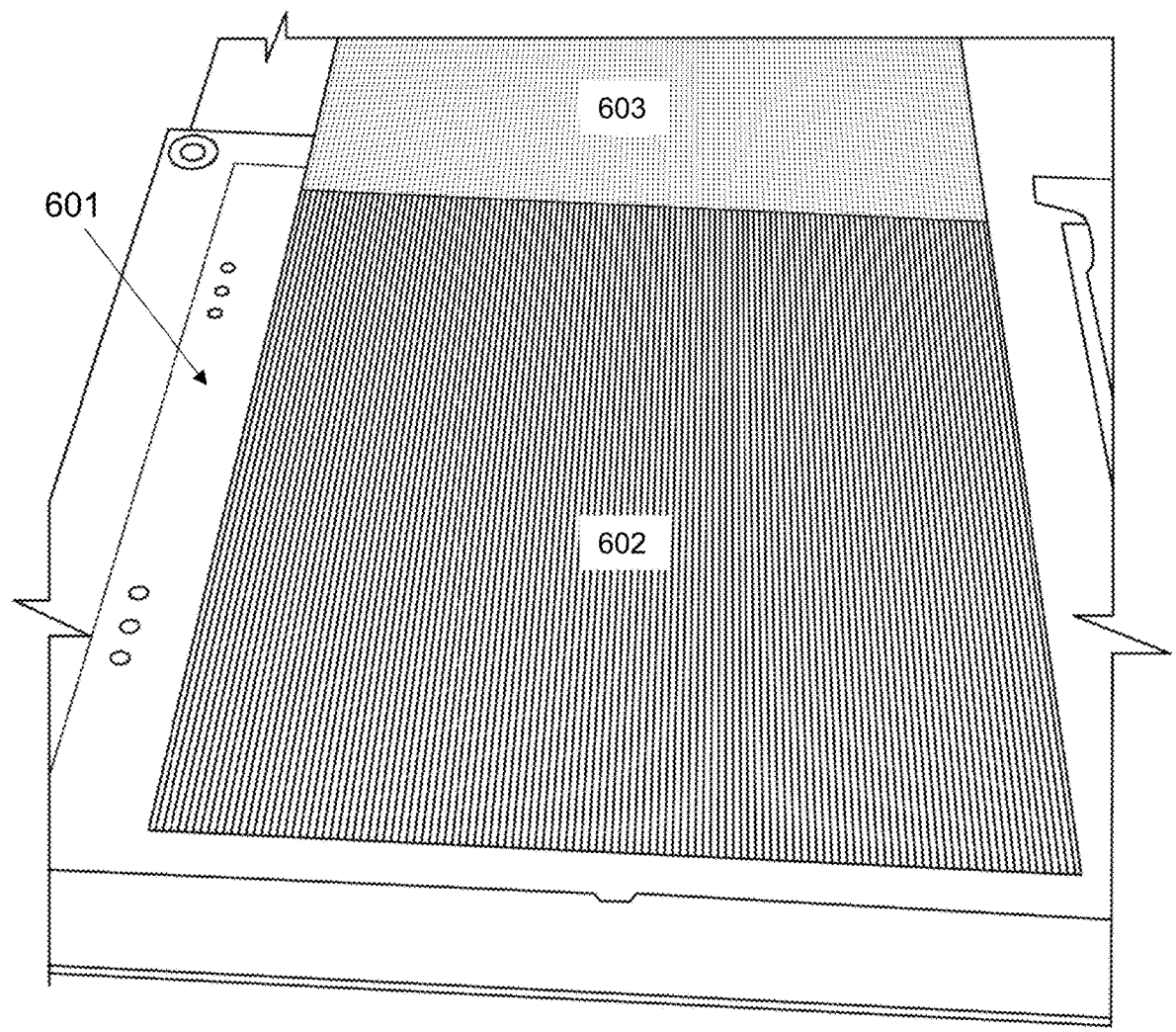
FIG. 6 shows vertical scintillating fiber detectors being installed in a tracking frame, wherein scintillation light generated from proton tracks is guided towards the top and measured with photodetectors, in accordance with an embodiment of the invention.

The relationship between the detector coordinate system and the camera coordinate system can be established by constructing the tracker with a known positioning of a set of optical markers, preferably enough to define a rigid body, relative to the sensitive detector elements. For example, FIG. 4 shows optical markers (e.g. 402 in FIG. 4) on a tracking frame, while FIG. 6 shows an example (600) of sensitive scintillating fiber detector elements (602, 603) inside the tracking frame (601). In the example (600) as illustrated in FIG. 6, the vertical scintillating fiber detectors (602, 603) are installed in the tracking frame (601), and scintillation light generated from proton tracks is guided towards the top and measured with photodetectors. A horizontal plane is placed directly on top of the plane shown in FIG. 6, so each tracker provides X-Y coordinates for proton tracks using orthogonal fibers rigidly positioned in the frame.

Figure 7:
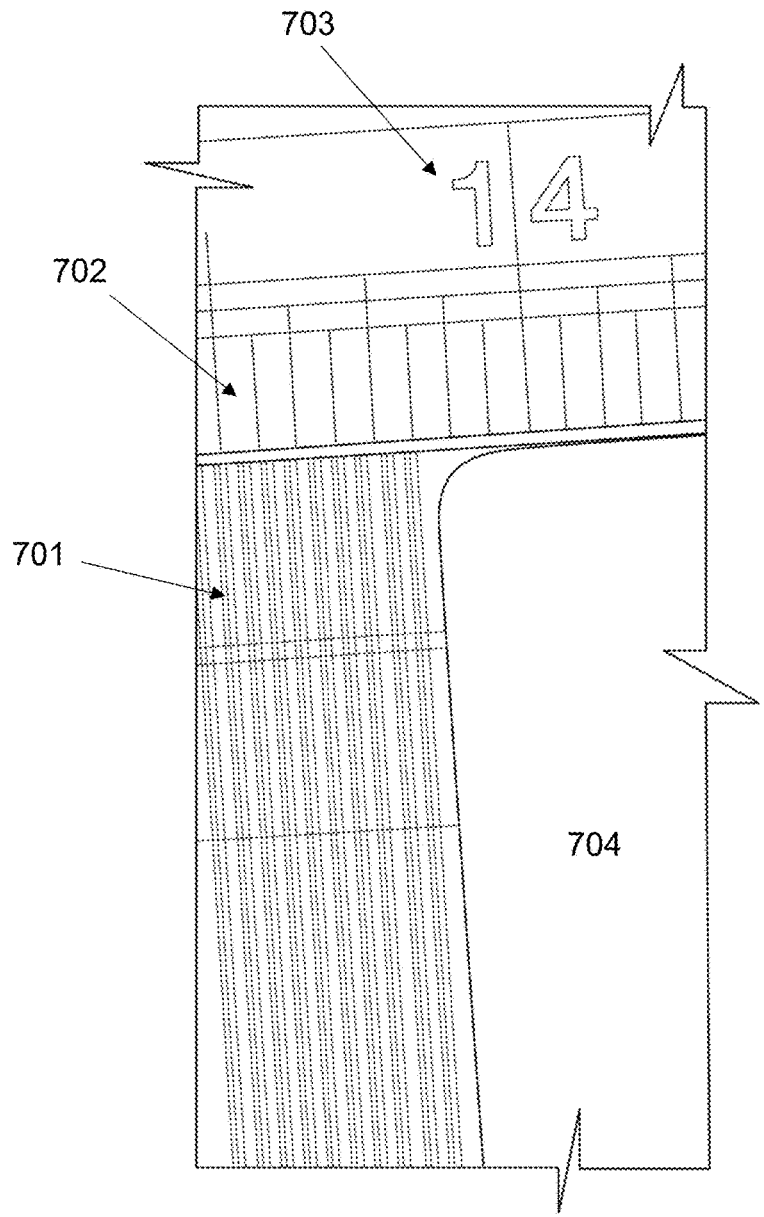
FIG. 7 shows a close-up view of fibers adjacent to a frame, with each fiber and each optical marker having a definite position relative to the frame, in accordance with an embodiment of the invention.

Furthermore, FIG. 7 shows a close-up view (700) of scintillating fibers (701) adjacent to a tracking frame (704). In a preferred embodiment of the invention, each fiber has a definite position relative to the tracking frame (704), and the optical markers (702, 703) have a definite position on the frame (704). The fiber positions can then be related to a camera coordinate system defined by these markers (702, 703) on the tracking frame (704). This enables a very simple relationship between the camera coordinate system and the tracker coordinate system.

The placement of the fibers (701) can be precisely known relative to the optical markers (702, 703), thus providing a link between the camera coordinate system and the tracker coordinate system. Conveniently, software such as Optitrack allows the definition of the camera coordinate system to be based on a rigid body. By utilizing these optical markers (702, 703) on the tracking frame (704), the camera coordinate system can be adjusted to coincide directly with the corners of the tracking plane.

Figure 8:
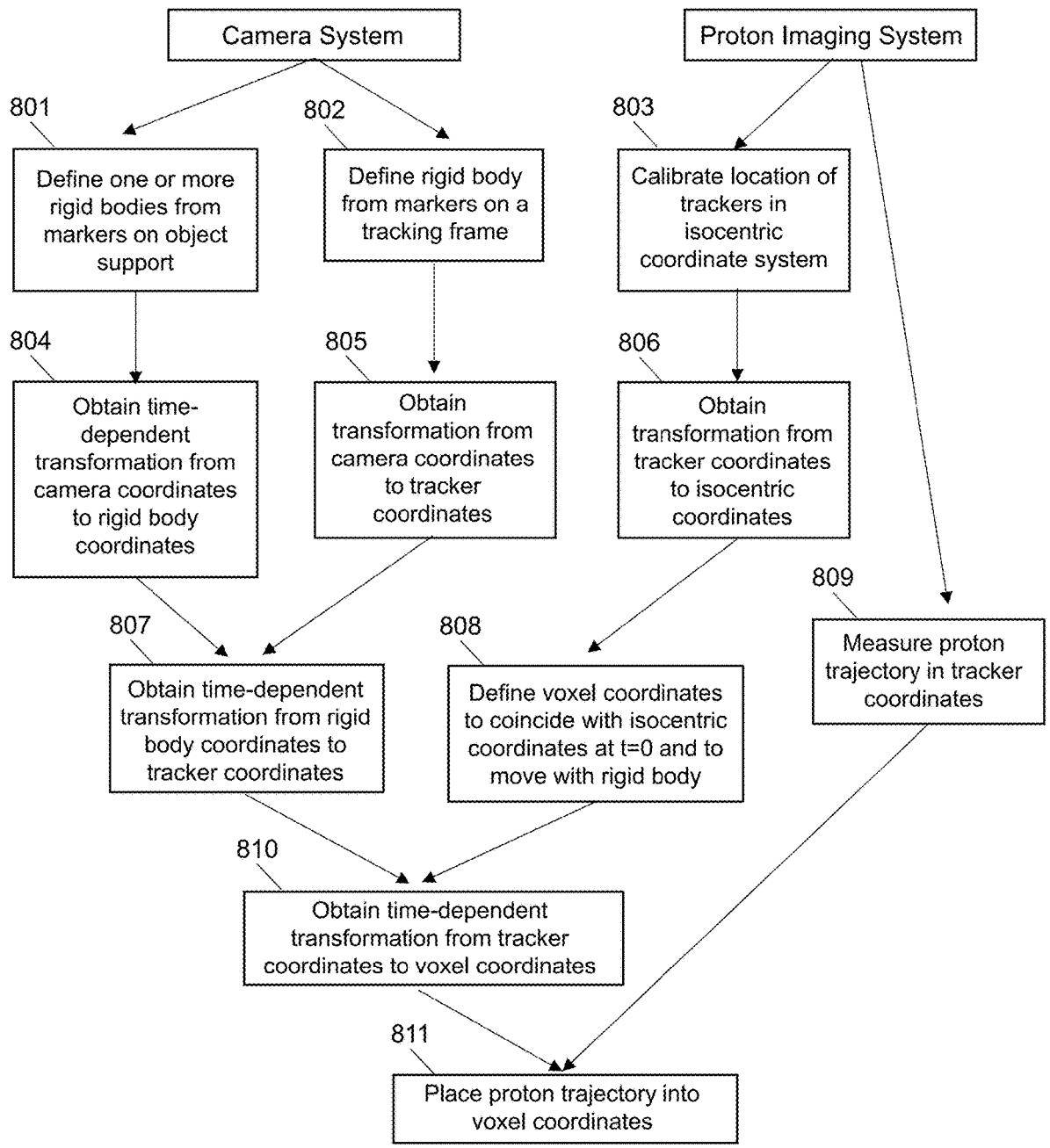
FIG. 8 shows a flowchart displaying an embodiment of a novel method to place a measured trajectory into a voxel system using a camera system, in accordance, in accordance with an embodiment of the invention.

After creating a correlated link between the tracking detector (e.g. from a pCT imaging system) and the camera coordinate system, standard coordinate transformation methods can be utilized to place proton trajectories into the voxel space. An operating flowchart (800) is shown in FIG. 8, with analysis of the camera system linked to the pCT imaging system, and the voxel space chosen to coincide with isocentric coordinates at t=0. The camera system and markers can be used to relate, standardize, and unify various coordinate systems from a tracker, a camera, a rigid body, and a voxel space. In this embodiment of the invention, the voxel grid is chosen to coincide with the isocentric coordinate system at t=0, but the isocentric coordinate system is not generally required or necessary to implement various embodiments of the present invention.

The operating flowchart (800) in FIG. 8 shows an implementation example that utilizes a camera system to place a measured trajectory into a voxel system. In this embodiment of the invention, the camera system is configured to define one or more rigid bodies from markers on an object support (801), and is also configured to define such rigid bodies from markers on a tracking frame (802), as shown in the operating flowchart (800). Meanwhile, a proton imaging system utilized in conjunction with the camera system can calibrate the location of trackers in an isocentric coordinate system (803), obtain coordinate transformation from tracker coordinates to isocentric coordinates (806), and then define voxel coordinates to coincide with isocentric coordinates at the beginning of measurement (i.e. t=0), wherein the voxel coordinates can be further plotted for any movements associated with the rigid body (808).

As illustrated in the operating flowchart (800) in FIG. 8, the camera system obtains a time-dependent coordinate transformation from camera coordinates to rigid body coordinates (804). The coordinate transformation from camera coordinates to tracker coordinates (805) is defined by the construction of the tracker system and the placement of optical markers. For example, markers (402) may be conveniently coplanar with the tracking plane, and commercial optical tracking software (e.g. Optitrack) typically enables the option of choosing three of these markers to define the camera coordinate system, as described in previous paragraphs. In this case, the coordinate transformation from camera coordinates may involve a simple set of offsets in cartesian coordinates x, y and z from the camera coordinates. These offsets may be determined, for example, by the methods described in conjunction with FIGS. 6, 7 and 10. Subsequently, a time-dependent coordinate transformation from the rigid body coordinates to the tracker coordinates is completed (807), with the known time-dependent coordinate transformation from the camera coordinates to the rigid body coordinates (804), and with the known transformation from the camera coordinates to the tracker coordinates (805).

Then, with all pertinent information derived from the time-dependent coordinate transformation from the rigid body coordinates to the tracker coordinates (807) and the voxel coordinates coinciding with the isocentric coordinates at t=0 (808), a time-dependent coordinate transformation from the tracker coordinates to the voxel coordinates can be obtained (810). With a proton trajectory measured in the tracker coordinates (809) from the proton imaging system, the camera system is now able to place a measured trajectory into a voxel system by placing the proton trajectory into the voxel coordinates (811), as illustrated in the operating flowchart (800) in FIG. 8.

Figure 9:
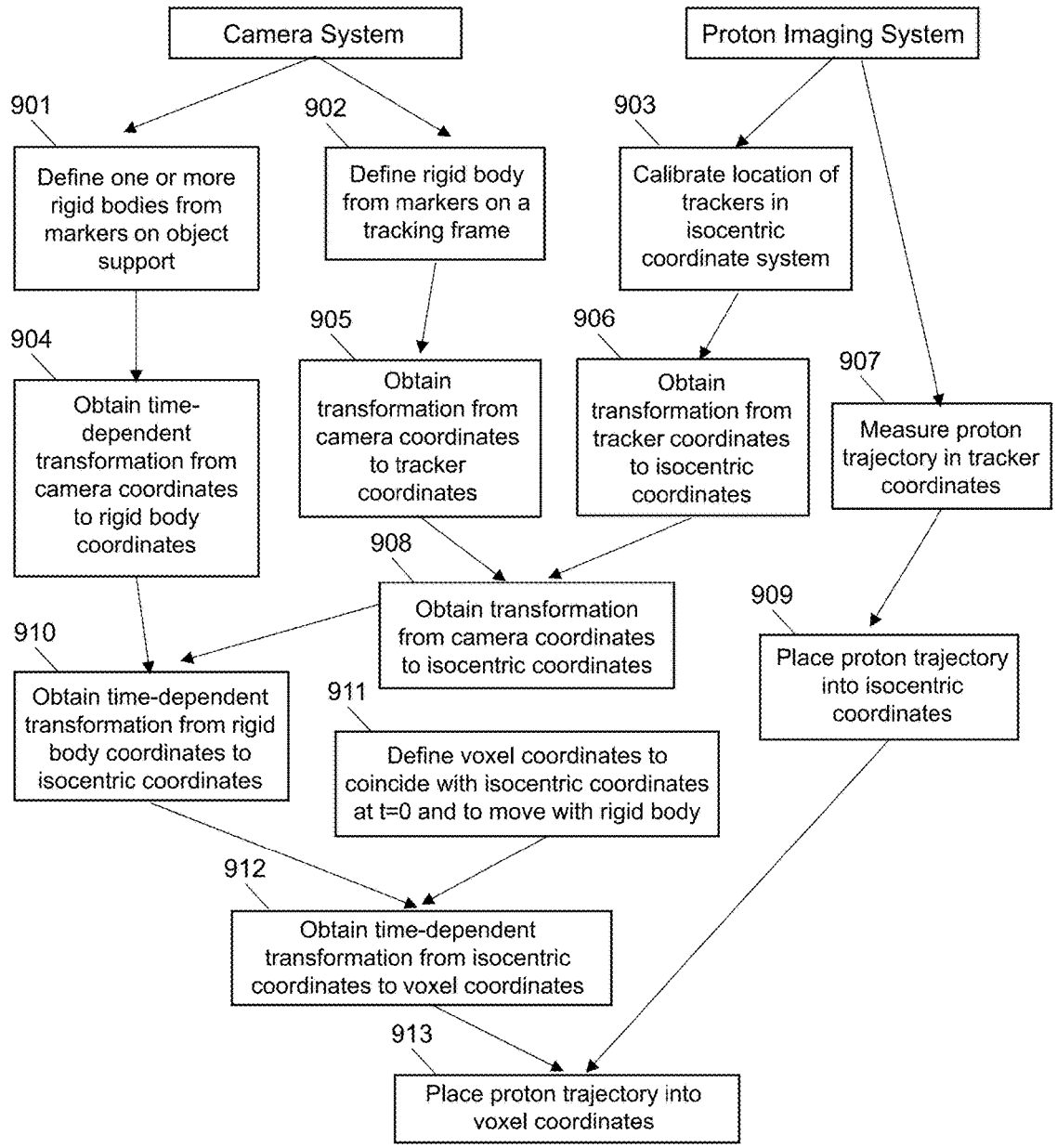
FIG. 9 shows an alternate flowchart of the novel method to utilize isocentric coordinates at an earlier stage of the multi-coordinate standardization processing to place a measured trajectory into a voxel system using a camera system, in accordance with an embodiment of the invention.

FIG. 9 shows an alternate operating flowchart (900) of the novel method to utilize isocentric coordinates at an earlier stage of the multi-coordinate standardization processing to place a measured trajectory into a voxel system using a camera system, in accordance with an embodiment of the invention. Though not essential, if the isocentric coordinates are to be utilized in an embodiment of the invention, it may be convenient to incorporate them at an earlier stage, as shown in this alternate operating flow chart (900).

In this alternate embodiment of the invention, the camera system is configured to define one or more rigid bodies from markers on an object support (901), and is also configured to define such rigid bodies from markers on a tracking frame (902), as shown in the alternate operating flowchart (900). Meanwhile, a proton imaging system utilized in conjunction with the camera system can calibrate the location of trackers in an isocentric coordinate system (903) and obtain coordinate transformation from tracker coordinates to isocentric coordinates (906).

As illustrated in the alternate operating flowchart (900) in FIG. 9, the camera system obtains a time-dependent coordinate transformation from camera coordinates to rigid body coordinates (904), and also obtains a coordinate transformation from camera coordinates to tracker coordinates (905). At this stage, the coordinate transformations from the camera coordinates to the isocentric coordinates (908) are readily achieved with the known transformation information from the camera coordinates to the tracker coordinates (905) in the camera system, and with the known transformation information from the tracker coordinates to the isocentric coordinates (906) in the proton imaging system.

Then, with the known coordinate transformation information from the camera coordinates to the isocentric coordinates (908) and the known time-dependent coordinate transformation from the camera coordinates to the rigid body coordinates (904), a time-dependent coordinate transformation from the rigid body coordinates to the isoentric coordinates (910) is obtained. Furthermore, voxel coordinates can be defined to coincide with the isocentric coordinates at the beginning of measurement (i.e. t=0), wherein the voxel coordinates can be further plotted for any movements associated with the rigid body (911).

Then, with all pertinent information derived from the time-dependent coordinate transformation from the rigid body coordinates to the isocentric coordinates (910) and the voxel coordinates coinciding with the isocentric coordinates at t=0 (911), a time-dependent coordinate transformation from the isocentric coordinates to the voxel coordinates can be obtained (912). With a proton trajectory measured in the tracker coordinates (907) and placed into the isocentric coordinates (909) by the proton imaging system, the camera system is now able to place a measured trajectory into a voxel system by placing the proton trajectory into the voxel coordinates (913), as illustrated in the alternate operating flowchart (900) in FIG. 9.

Figure 10:
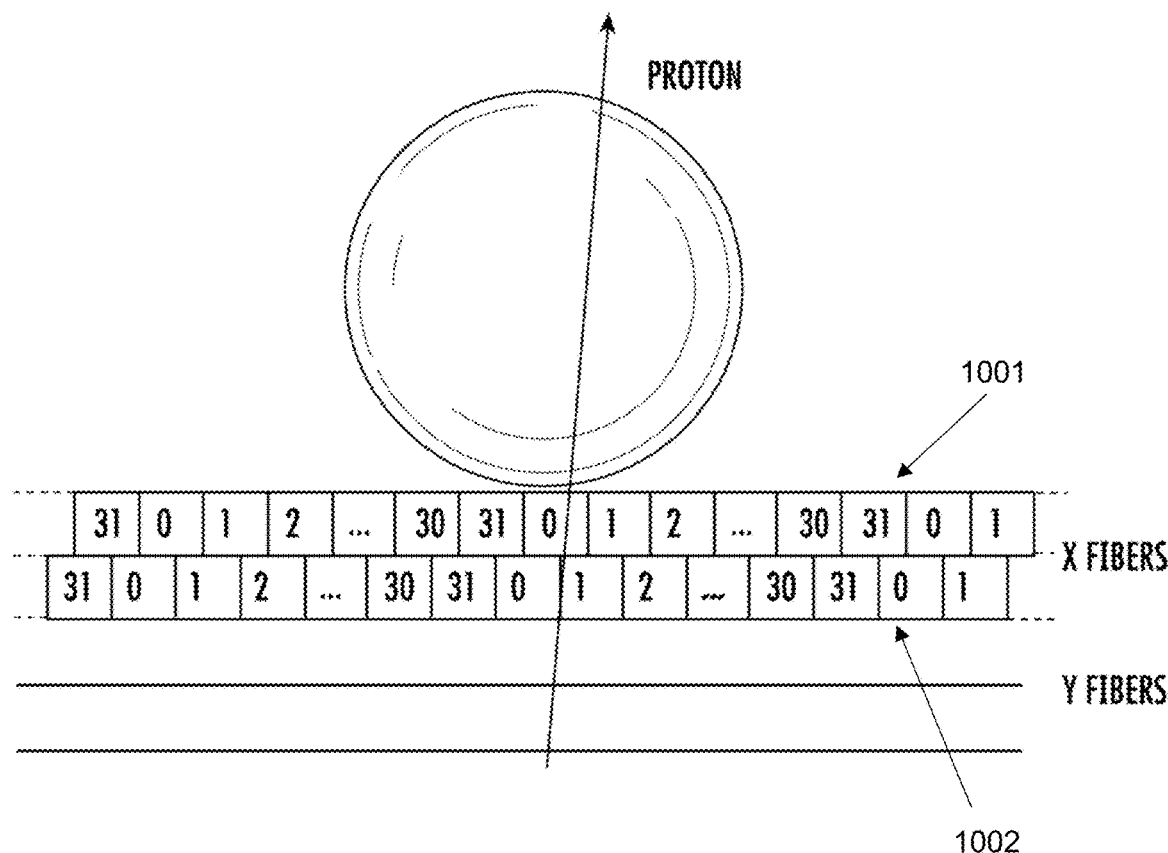
FIG. 10 shows markers placed on tracking plane during a test that can be seen simultaneously by both the proton imaging system and the camera system, which provides a check of the relation between the coordinate systems, in accordance with an embodiment of the invention.

FIG. 10 shows an example (1000) of markers (1001, 1002) being placed on a tracking plane during a test that can be seen simultaneously by both the proton imaging system and the camera system, wherein the markers (1001, 1002) provide a check of the relation between the coordinate systems, in accordance with an embodiment of the invention. While the markers (402) shown in FIG. 4 are placed outside the sensitive area of the tracking plane, it is possible to validate and test the coordinate transformations by taking an image with one or more markers (1001, 1002) placed on the surface of the sensitive area of the tracking plane, as illustrated in FIG. 10.

The markers (1001, 1002) in FIG. 10 are visible both with the proton imaging system and the camera system independently. If the coordinates of these systems are correctly linked, the position of the marker as measured in the detector system should agree with the position measured by the camera system. The technique to correlate two disparate coordinate systems (i.e. imaging detector system coordinates and camera-based optical tracking coordinates) can also be applied to various medical imaging detector systems other than proton imaging, as long as the placement of a set of optical markers can be related to the position of sensitive detector elements.

Figure 11:
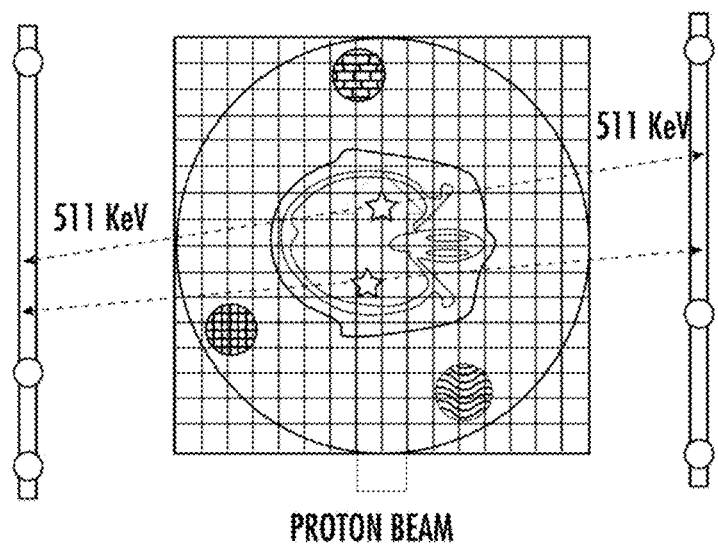
FIG. 11 shows an alternate example that utilizes positron emission tomography (PET) detectors in proton therapy systems, in accordance with an embodiment of the invention.
Figure 11:
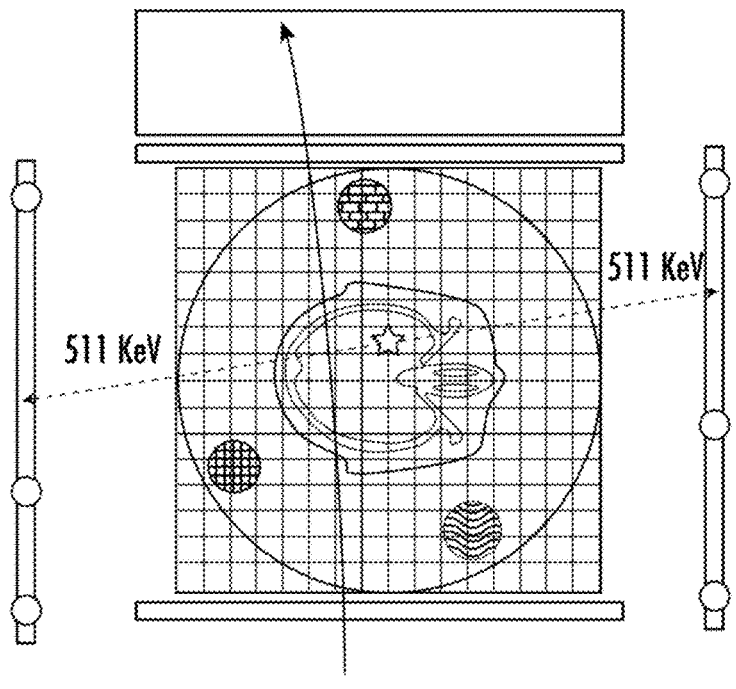

FIG. 11 shows an alternate example with two image diagrams (1100A, 1100B) that utilize positron emission tomography (PET) detectors in a proton therapy system, in accordance with an embodiment of the invention. Both image diagrams (1100A, 1100B) in FIG. 11 show panels on each side of an object, which detect back-to-back 511 KeV gamma rays from the annihilation of a positron. Each panel contains an array of detecting elements, and the positron annihilation can be determined to have occurred somewhere on a line connecting two of these elements. The position of the line in the detector system can be related to the camera system with optical markers on the panel frames, which have a definite relationship to the detector element positions.

The upper image diagram (1100A) in FIG. 11 illustrates positron emitters produced by nuclear interactions of a therapeutic proton beam with a patient can be detected and provide information on the range of the proton beam. The lower image diagram (1100B) in FIG. 11 illustrates positron emitters from an injected substance (e.g. fluorodeoxyglucose (FDG)), which accumulates in tumors, being imaged with a rotating patient to produce a PET image. In this case, a pCT image can be simultaneously produced, using the camera system to relate the object. The PET system and the pCT system can then produce a combined PET-pCT image. A PET-CT image could be analogously produced.

A computed tomography (CT) scanner can also utilize an embodiment of the present invention to combine data sets with the patient couch in different positions. Normally, a CT scanner uses a single patient position. The use of our techniques would enable combining data using more than one patient position. For example, if the patient is on a couch, the field of view of the CT scanner could effectively be increased by combining scans with lateral or vertical movements of the couch relative to the CT rotation axis. In another instance, combining scans taken with different couch angles may enable a lower noise image for the same dose by spreading the x-ray measurements out over more directions.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the claims presented herein.

What is claimed is:

1. A method for registering an optical tracking system with a particle detector system in a common voxel coordinate grid to improve quality assurance, accuracy, speed, and operating cost efficiencies of a medical imaging process, the method comprising the steps of:

defining, with a camera system as the optical tracking system, a rigid body from a first set of markers on an object support and a second set of markers on a tracking frame;

obtaining, with the camera system, a time-dependent coordinate transformation from camera coordinates to rigid body coordinates;

obtaining, with the camera system, a coordinate transformation from the camera coordinates to tracker coordinates of the tracking frame;

obtaining, with the camera system, a time-dependent coordinate transformation from the rigid body coordinates to the tracker coordinates;

calibrating, with a proton imaging system as the particle detector system, locations of trackers in an isocentric coordinate system;

obtaining, with the proton imaging system, a coordinate transformation from the tracker coordinates to isocentric coordinates in the isocentric coordinate system;

defining, with the proton imaging system, voxel coordinates of the common voxel coordinate grid to coincide with the isocentric coordinates at a beginning of measurement, wherein the voxel coordinates move with the rigid body;

obtaining, with the camera system and the proton imaging system, a time-dependent coordinate transformation from the tracker coordinates to the voxel coordinates;

measuring, with the proton imaging system, a proton trajectory in the tracker coordinates; and placing the proton trajectory into the voxel coordinates of the common voxel coordinate grid by utilizing the time-dependent coordinate transformation from the tracker coordinates to the voxel coordinates and the proton trajectory measured by the proton imaging system.

2. The method of claim 1, wherein the camera system and the proton imaging system are utilized together for registering in the common voxel coordinate grid during a proton imaging procedure or a proton therapy procedure for a patient positioned on the object support.

3. The method of claim 1, wherein the camera system and the proton imaging system further utilizes positron emission tomography (PET) detectors as an integrated part of a proton therapy system.

4. The method of claim 1, wherein the proton trajectory is characterized by a proton pencil beam scanning (PBS) that emerge from a focal point with a diverging pattern, wherein a steering of a pencil beam is calibrated to be directed at the isocentric coordinates between tracking detector panels.

5. The method of claim 4, wherein the diverging pattern and the steering of the pencil beam in the proton PBS are utilized to register the tracker coordinates with the isocentric coordinates.

6. A method for registering an optical tracking system with a particle detector system in a common voxel coordinate grid to improve quality assurance, accuracy, speed, and operating cost efficiencies of a medical imaging process, the method comprising the steps of:

defining, with a camera system as the optical tracking system, a rigid body from a first set of markers on an object support and a second set of markers on a tracking frame;

obtaining, with the camera system, a time-dependent coordinate transformation from camera coordinates to rigid body coordinates;

obtaining, with the camera system, a coordinate transformation from the camera coordinates to tracker coordinates of the tracking frame;

calibrating, with a proton imaging system as the particle detector system, locations of trackers in an isocentric coordinate system;

obtaining, with the proton imaging system, a coordinate transformation from the tracker coordinates to isocentric coordinates in the isocentric coordinate system;

obtaining, with the camera system and the proton imaging system, a coordinate transformation from the camera coordinates to the isocentric coordinates;

obtaining, with the camera system, a time-dependent coordinate transformation from the rigid body coordinates to the isocentric coordinates;

defining voxel coordinates of the common voxel coordinate grid to coincide with the isocentric coordinates at a beginning of measurement, wherein the voxel coordinates move with the rigid body;

obtaining a time-dependent coordinate transformation from the isocentric coordinates to the voxel coordinates;

measuring, with the proton imaging system, a proton trajectory in the tracker coordinates;

placing, with the proton imaging system, the proton trajectory into the isocentric coordinates; and placing the proton trajectory into the voxel coordinates of the common voxel coordinate grid by utilizing the time-dependent coordinate transformation from the isocentric coordinates to the voxel coordinates and the proton trajectory in the isocentric coordinates.

7. The method of claim 6, wherein the camera system and the proton imaging system are utilized together for registering in the common voxel coordinate grid during a proton imaging procedure or a proton therapy procedure for a patient positioned on the object support.

8. The method of claim 6, wherein the camera system and the proton imaging system further utilizes positron emission tomography (PET) detectors as an integrated part of a proton therapy system.

9. The method of claim 6, wherein the proton trajectory is characterized by a proton pencil beam scanning (PBS) that emerge from a focal point with a diverging pattern, wherein a steering of a pencil beam is calibrated to be directed at the isocentric coordinates between tracking detector panels.

10. The method of claim 9, wherein the diverging pattern and the steering of the pencil beam in the proton PBS are utilized to register the tracker coordinates with the isocentric coordinates.

* * * * *